United States Patent
St. John et al.

(10) Patent No.: US 8,422,634 B2
(45) Date of Patent: Apr. 16, 2013

(54) AUTOMATED MEDICAL IMAGING SYSTEM FAULT DETECTION

(75) Inventors: Daniel St. John, Crystal Lake, IL (US); Thomas Ruggiero, Schaumburg, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 381 days.

(21) Appl. No.: 12/916,732

(22) Filed: Nov. 1, 2010

(65) Prior Publication Data

US 2011/0170667 A1 Jul. 14, 2011

Related U.S. Application Data

(60) Provisional application No. 61/294,968, filed on Jan. 14, 2010.

(51) Int. Cl.
 *H05G 1/08* (2006.01)
 *H05G 1/00* (2006.01)

(52) U.S. Cl.
 USPC .............................. 378/91; 378/204; 378/901

(58) Field of Classification Search ............. 378/91, 378/92, 98, 167, 204, 210, 901; 710/15, 710/19, 100, 104–106; 709/217–219, 223, 709/224, 245, 246, 249, 250, 253; 715/733–736, 715/764
See application file for complete search history.

(56) References Cited

U.S. PATENT DOCUMENTS

| | | | |
|---|---|---|---|
| 6,275,559 B1 | 8/2001 | Ramani et al. | |
| 7,142,636 B2 | 11/2006 | Hsieh et al. | |
| 7,334,160 B2* | 2/2008 | Gudapakkam et al. | 714/31 |
| 2003/0095144 A1* | 5/2003 | Trevino et al. | 345/764 |
| 2003/0135389 A1 | 7/2003 | Gudapakkam et al. | |
| 2005/0063513 A1 | 3/2005 | Hsieh et al. | |
| 2005/0197860 A1 | 9/2005 | Joffe et al. | |
| 2006/0104536 A1 | 5/2006 | Hsieh et al. | |
| 2007/0007453 A1 | 1/2007 | Graw et al. | |
| 2007/0011295 A1* | 1/2007 | Hansen | 709/223 |

\* cited by examiner

*Primary Examiner* — Anastasia Midkiff
(74) *Attorney, Agent, or Firm* — Alexander J Burke (57) ABSTRACT

A system automatically detects and reports a hardware and/or software error in an X-ray system. A system automatically detects and identifies failed components of a distributed X-ray imaging system. Multiple different subsystems of an X-ray imaging system individually include, an executable procedure for detecting a failed component in a respective subsystem and a communication interface for initiating generation and communication of a message identifying the failed component and identifying the respective subsystem including the failed component. A repository stores data identifying failed components within the multiple different subsystems in response to the communicated message. An error processor accesses the repository of data and provides composite information enabling a user to identify failed components within an X-ray imaging system.

17 Claims, 5 Drawing Sheets

AUTOMATED MEDICAL IMAGING SYSTEM FAULT DETECTION

This is a non-provisional application of provisional application Ser. No. 61/294,968 filed 14 Jan. 2010, by D. St. John et al.

FIELD OF THE INVENTION

This invention concerns a system for automatic detection and identification of failed components of a distributed X-ray imaging system, for example.

BACKGROUND OF THE INVENTION

An X-ray imaging system includes multiple hardware and software subsystems. Each of these subsystems is typically divided into components. Many of these subsystems are embedded systems that have little or no storage capability and limited error reporting capability. When there is a problem in the field, multiple people associated with different subsystems are needed to investigate an issue, (e.g. an error or failure) involving review of scattered, distributed and disjointed log information to ascertain where an error occurred and why. This often involves an engineer thus limiting the effectiveness and timeliness of repairs in the field and resulting in engineering personnel working with field service to recreate different scenarios to determine what might have happened to cause an error. X-Ray imaging system components comprise multiple sub-components which are employed by X-ray system operational processes and typically lack a capability to store status and error data. A system according to invention principles addresses these deficiencies and associated problems.

SUMMARY OF THE INVENTION

A system automatically detects and reports a hardware and/or software error in an X-ray imaging system and graphically indicates on a display a particular component that has experienced the failure to facilitate and accelerate diagnosis and correction of the fault. A system automatically detects and identifies failed components of a distributed X-ray imaging system. Multiple different subsystems of an X-ray imaging system individually include, an executable procedure for detecting a failed component in a respective subsystem and a communication interface for initiating generation and communication of a message identifying the failed component and identifying the respective subsystem including the failed component. A repository stores data identifying failed components within the multiple different subsystems in response to the communicated message. An error processor accesses the repository of data and provides composite information enabling a user to identify failed components within an X-ray imaging system.

DETAILED DESCRIPTION OF THE INVENTION

The inventor has advantageously recognized the need for a system to automatically detect and report a failure in a medical imaging system and that this may be facilitated by use of particular communication protocols such as an sRIO protocol. The Serial RapidIO (SRIO) protocol standard and associated RapidIO specification is a packet-based protocol that is employed by endpoints, which originate and process digital data packets and is employed by switches, which are used to connect endpoints. RapidIO is a layered specification, divided into a physical layer protocol, packet transport (routing) protocol and multiple protocols in a logical layer. An sRIO message is employed as part of this protocol. Subsystems are connected to an sRIO network as endpoints. A system according to invention principles in one embodiment advantageously employs the sRIO protocol and sRIO message capability, for example, to automatically detect and report a failure.

Figure 1:
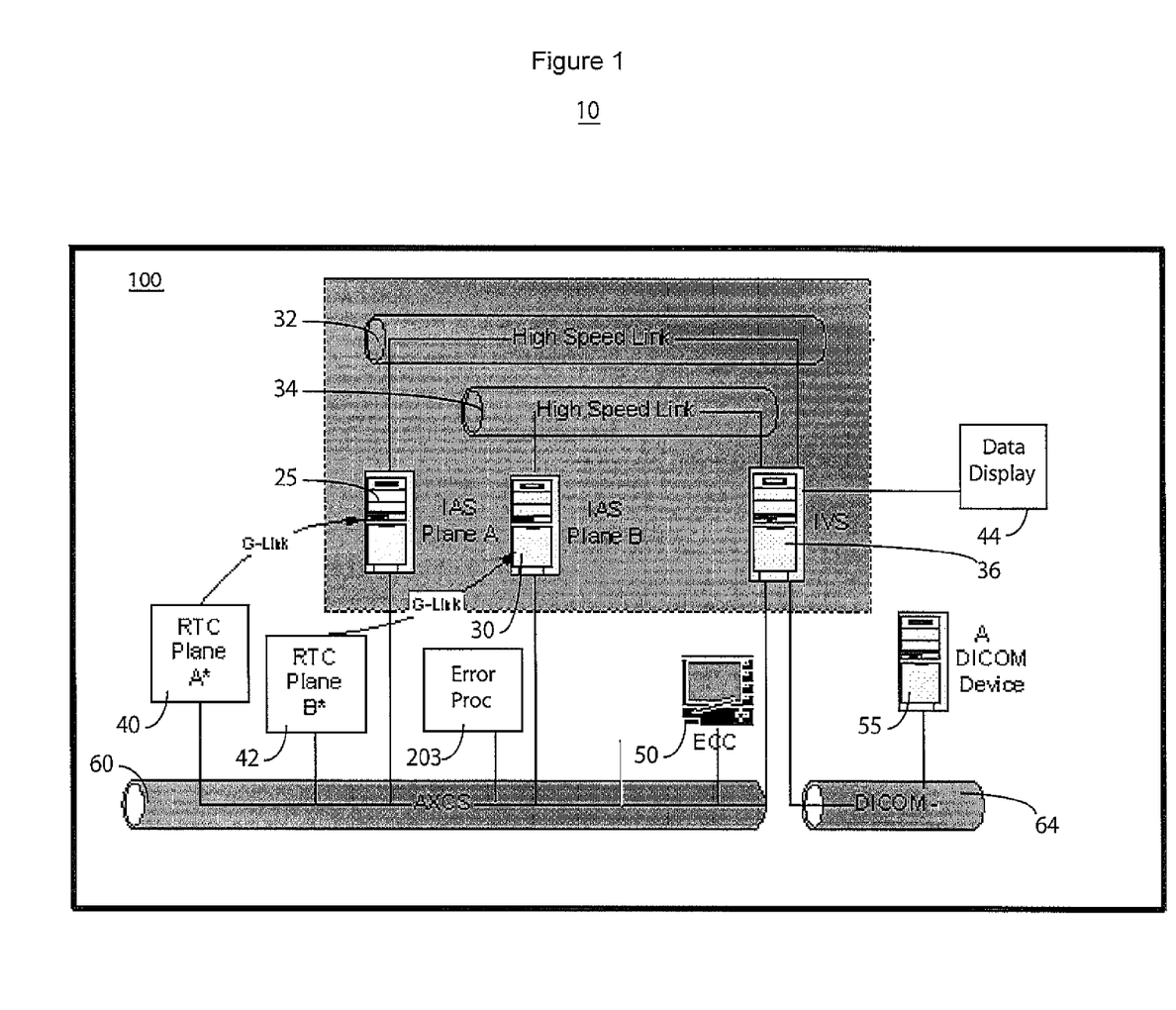
FIG. 1 shows an X-ray system including a system for automatically detecting and identifying failed components of a distributed X-ray imaging system, according to invention principles.

FIG. 1 shows a biplane X-ray system 100 including an error processing unit 203 for automatically detecting and identifying failed components of a distributed X-ray imaging system. System 100 includes biplane image acquisition systems 25 and 30 for acquiring X-ray images that are linked via relatively high speed links 32 and 34 respectively, with image validation system 36 for post processing images for storage in DICOM format in DICOM storage device 55 via link 64. Biplane image acquisition systems 25 and 30 communicate with imaging laboratory devices on computer system network 60 via receiver transmitter components 40 and 42 respectively. Imaging laboratory devices on computer system network 60 include error processing unit 203 and control console 50. Display device 44 is controlled by IVS 36 and presents medical images and display images comprising a Graphical User Interface (GUI) responsive to user commands entered via a data entry device of control console 50. The display images are generated in response to predetermined user (e.g., physician) specific preferences. At least one repository comprising DICOM device 55, for example, stores medical image studies for multiple patients in DICOM compatible (or other) data format. A medical image study individually includes multiple image series of a patient anatomical portion which in turn individually include multiple images. Biplane image acquisition systems 25 and 30 as well as image validation system 36 also communicate with imaging laboratory devices on computer system network 60 via direct bidirectional communication links.

Error processing unit 203 automatically detects and identifies failed components of distributed X-ray imaging system 100. Multiple different subsystems of X-ray imaging system 100 individually include, an executable procedure for detecting a failed component in a respective subsystem and a communication interface for initiating generation and communication of a message identifying the failed component and identifying the respective subsystem including the failed component. A repository of data in error processing unit 203 stores data identifying failed components within the multiple different subsystems in response to the communicated message. An error processor in unit 203 accesses the repository of data and provides composite information enabling a user to identify failed components within X-ray imaging system 100.

Figure 2:
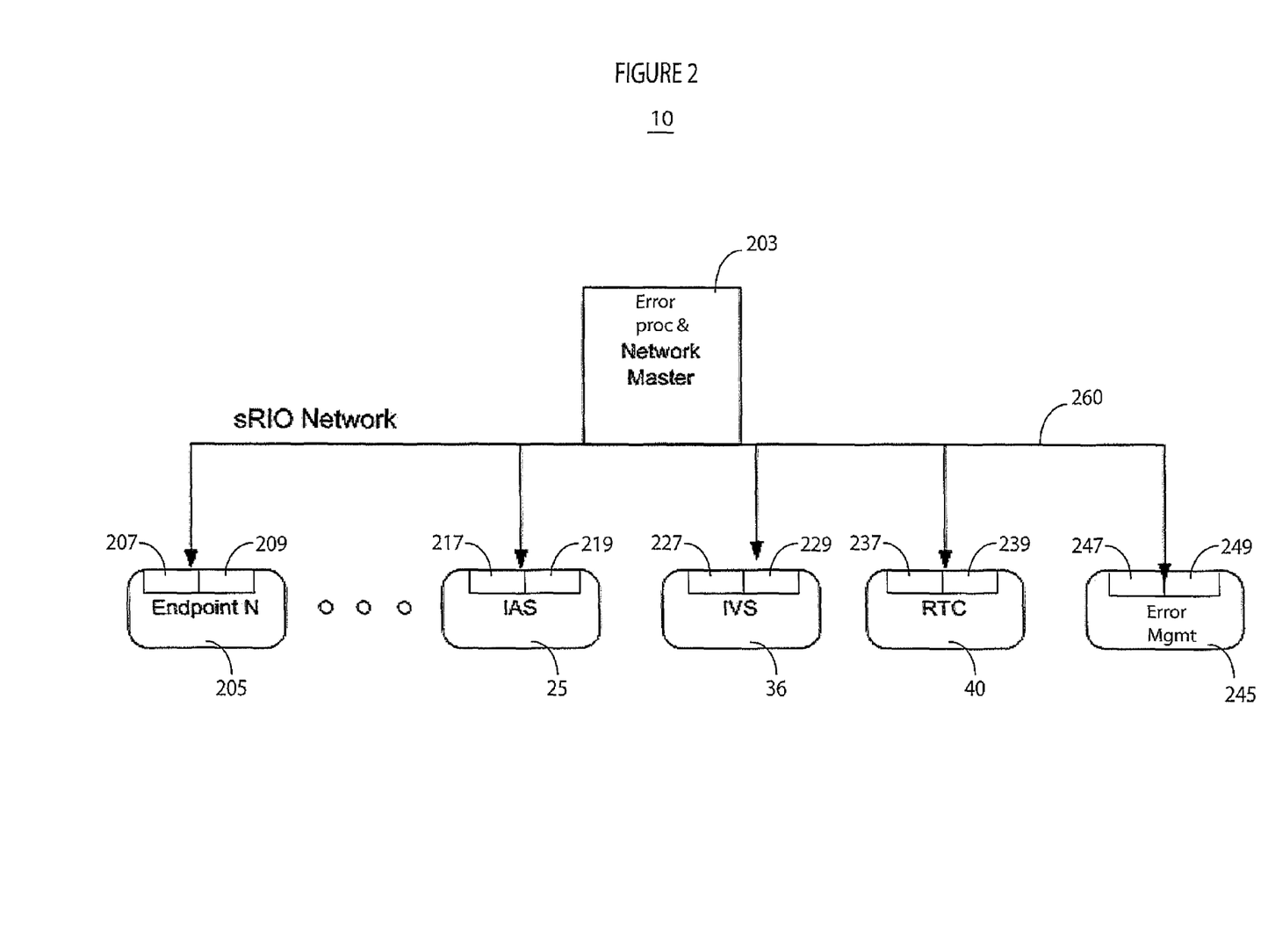
FIG. 2 shows a networked system for automatically detecting and identifying failed components of a distributed X-ray imaging system, according to invention principles.

FIG. 2 shows networked system 10 for automatically detecting and identifying failed components of distributed X-ray imaging system 100 (FIG. 1). Error processing unit 203 comprises a Network Master component that controls networked system 10 topology and routing of messages within imaging system 100. Some components of X-ray imaging system 100, such as RTC units 40 and 42 and the Network Master unit do not contain disk drives or other long term storage means which renders capture of status and error data difficult. Multiple subsystems within X-ray system 100 including subsystem endpoint N 205, image acquisition system 25, image validation system 36, receiver transmitter component 40 and error management system 245 are connected via sRIO communication protocol network 260, for example. The multiple subsystems 205, 25, 36, 40 and 245 within X-ray system 100 individually include, executable procedures 207, 217, 227, 237 and 247 respectively, for detecting a failed component in a respective subsystem. The multiple subsystems 205, 25, 36, 40 and 245 within X-ray system 100 also individually include, communication interfaces 209, 219, 229, 239 and 249 respectively, for initiating generation and communication of a message identifying the failed component and identifying the respective subsystem including the failed component.

The Network Master component in error processing unit 203 controls routing between each subsystem endpoint and manages the sRIO network. Error management unit 245 receives and stores error messages from subsystems 205, 25, 36, 40 and 245 and subsystem components in real-time using the sRIO message capability. A component such as an image acquisition component within the IAS (image acquisition system) 25 detects an error and reports that error to the Network Master component via a predetermined route. The Network Master component determines the source of a failure being reported from source identification data in an error message received from a subsystem. The Network Master component pre-pends an identifier identifying the subsystem reporting the failure, to a message including a description of the error, for communication to Error management system 245 for recording.

The Network Master component automatically generates and communicates a message identifying a detected subsystem fault to Error management system 245 using a predetermined message structure. The predetermined message structure includes, an identifier of a Failing Subsystem provided by the Network Master component, an identifier of a Failing Component within the Failing Subsystem derived from an sRIO message from the Failing Subsystem and a Textual description of the failure and system information provided in the sRIO message from the Failing Subsystem. System 10 uniquely identifies failing subsystems and components by storing data in error management system 245 (and unit 203) using an encoded message structure. An error processor in error processor unit 203 accesses a centralized repository of data in unit 203 or error management system 245 and provides composite information enabling a user to identify failed components within X-ray imaging system 100. System 10 also graphically identifies a failing subsystem and component within the subsystem in a warning message automatically presented in a display image on display 44 (FIG. 1). System 10 also uses an sRIO message function to report and store in a centralized location in unit 203 and unit 245 state information for use in determining the state of imaging system 100 and identifying events that have transpired in system 100 over a predetermined period of time and in chronological order, facilitating failure resolution.

Figure 3:
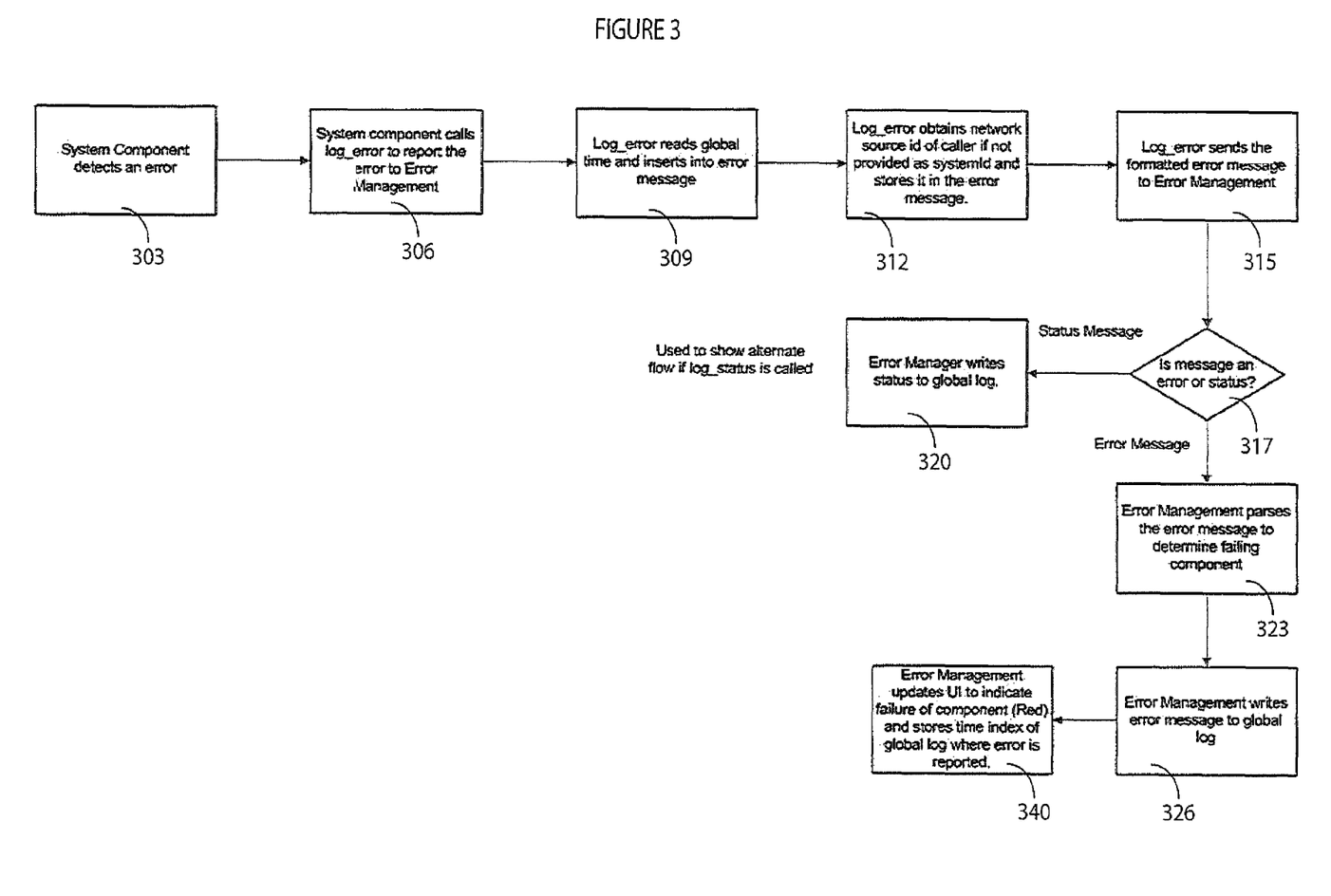
FIG. 3 shows a flowchart of a process used for acquiring and processing messages for automatically detecting and identifying failed components of a distributed X-ray imaging system, according to invention principles.

FIG. 3 shows a flowchart of a process used for acquiring and processing messages for automatically detecting and identifying failed components of a distributed X-ray imaging system. The flowchart shows processing from a time a subsystem component identifies an error until a user is notified of the error. System 10 employs a distributed architecture including a long term storage repository in units 203 and 245 as a repository of error and status information from subsystems. Error management system 245 comprises a long terms storage node that receives, parses and sequences error and status messages from subsystem components and graphically identifies reported errors in a display image. Error management system 245 provides global definitions of system components that the system is required to use for reporting purposes. It also provides shared executable procedures used by system 100 subsystems to report error messages (using a log_error procedure) and report status messages (using a log_status procedure).

In response to detection of a failed component in a subsystem of imaging system 100 in step 303 by use of an executable procedure, the subsystem uses a reporting log_error (or log-status) executable procedure for initiating generation and communication of a message identifying the failed component and identifying the subsystem including the failed component. In step 306 the log_error (or log-status) procedure formats and generates an error (or status) message including, an unsigned integer comprising a subsystem identifier, a text string process, a text string component and string status text. Specifically, the subsystem identifier is an identifier established by Error management system 245 (FIG. 2). Alternatively, this information is inserted by the Network Master when the message is sent. The text string process, text string component and string status text are text strings that the subsystem component determines. In step 309, the log_error (or log-status) procedure reads a global time from a shared location within system 10 network and creates a required error (or status) message including a time stamp and transports the error (or status) message data to a long term storage node across the distributed network of system 10 using a unit in the Error management system 245, for example.

The log_error executable procedure timestamps individual messages with a global time and error management system 245 (or error processing unit 203) collates and sequences error and status messages for individual subsystem components. A timestamp is used as a reference within an error log file so that error management system 245 is able to locate an exact line representing a failure in the subsystem in response to a user entered or system query. System 10 advantageously incorporates network transport logic within error processing unit 203 or error management unit 245 to support seamless operation by system 10 irrespective of network topology and implementation using routing information provided by the Network Master component.

In step 312, the log_error procedure determines a network source identifier of the calling failed subsystem and incorporates it in the error (or status) message if it is not already provided as the subsystem identifier in the generated message. In step 315, the log_error procedure communicates the formatted and generated error (or status) message to the error processing unit 203. Error processing unit 203 in step 317 determines from message identification data whether a received message is an error or status message and if it is a status message, stores the message in a global log in step 320. If it is an error message, error processing unit 203 in step 323 parses the received message to obtain data identifying the failed subsystem component. In step 326, error processing unit 203 communicates the error message to a global log in the error processing unit 203 and error management system 245. In step 340, error processing unit 203 updates a display image presented on display 44 (FIG. 1) to include data identifying a failed subsystem component and stores a timestamp and time identifier index of the failure message stored in the global log.

Figure 4:
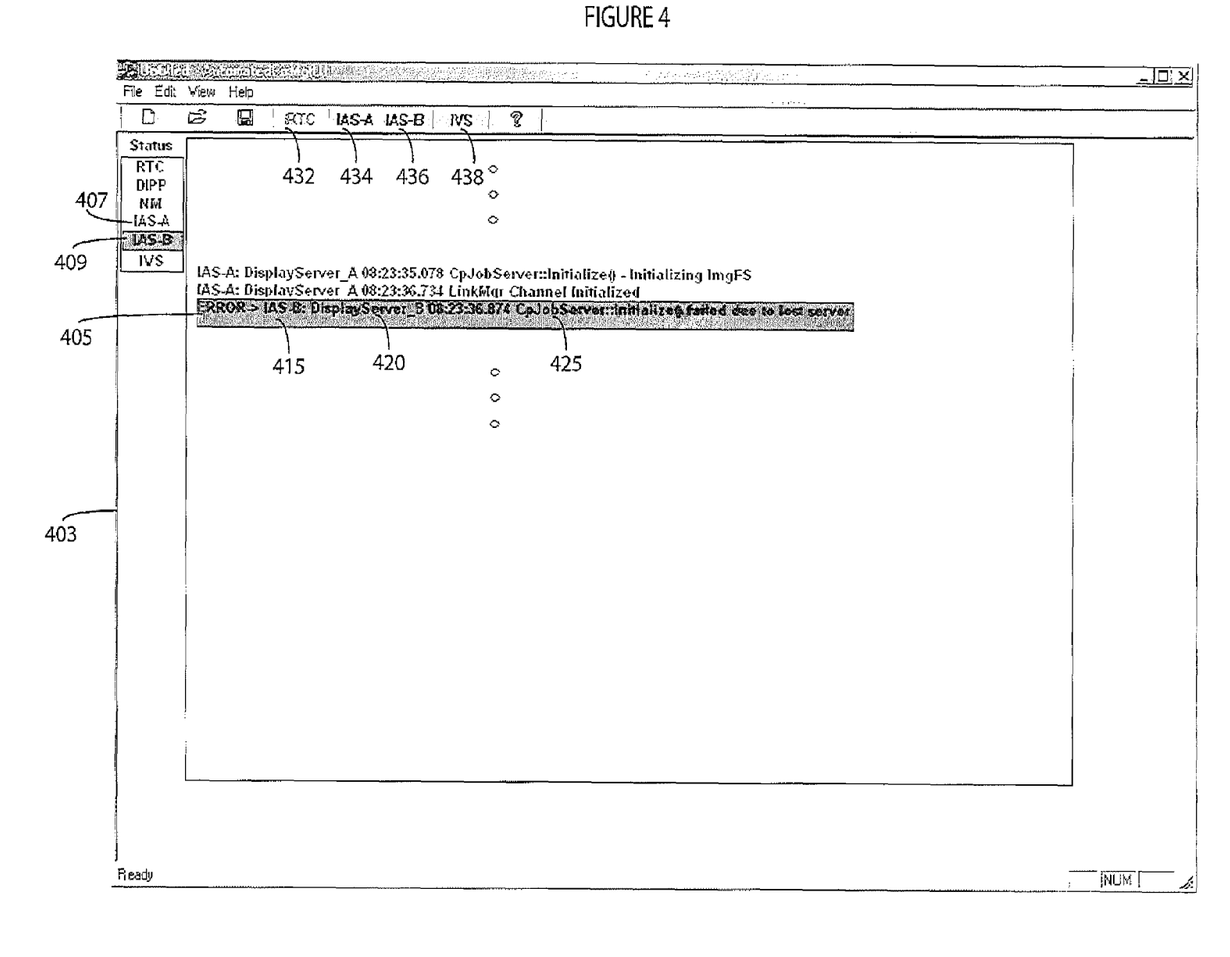
FIG. 4 shows a user interface display image for identifying status of system components and identifying failed components, according to invention principles.

FIG. 4 shows user interface display image 403 for identifying status of system components and identifying failed components with text e.g., text 405 indicating and describing, failure characteristics. Subsystem components such as image acquisition system A and image acquisition system B are identified in user interface 403 with labels 407 and 409 respectively, for example. Labels are shaded green if the associated subsystem is operational and in red for a subsystem having a detected failed component, for example. A user double clicks a displayed label of a particular failing component or text indicating characteristics of the failure to initiate presentation of an image window showing an error log file and data associated with the particular failing component as highlighted (e.g. by color, shading hatching, background or symbols, for example). A user is presented with additional details concerning other failed system components in the error log that may or may not have contributed to the failure of the particular failing component. This information is provided in a shared global error log and accelerates resolution of a failure by facilitating identification of a failure cause. The global error log highlights a failed component and related failed components to facilitate error resolution in the field as well as during a development cycle. Image acquisition system B is indicated as having an error in items 405 and 409. In response to a user selecting items 405 and 409 the global error log is displayed highlighting a log item corresponding to the failure of image acquisition system B. A log message contains a text identifier (IAS-B 415), which is populated in response to a received subsystem identifier. The log message also indicates a process (DisplayServer_B 420) and a sub-component failure being within (CIpJobServer 425) together with a timestamp identifying when the error occurred and entries in the log are ordered from top to bottom by time stamp with latest failures on top.

Button labels 432, 434, 436 and 438 identify imaging system 100 subsystems and enable a user to filter information displayed in the global error log. In response to a button identifying a particular subsystem being selected, corresponding failure messages of the particular subsystem are shown in the log presented on display 44 and failure messages of other subsystems are excluded. This enables a user to focus a failure investigation on a particular subsystem.

Figure 5:
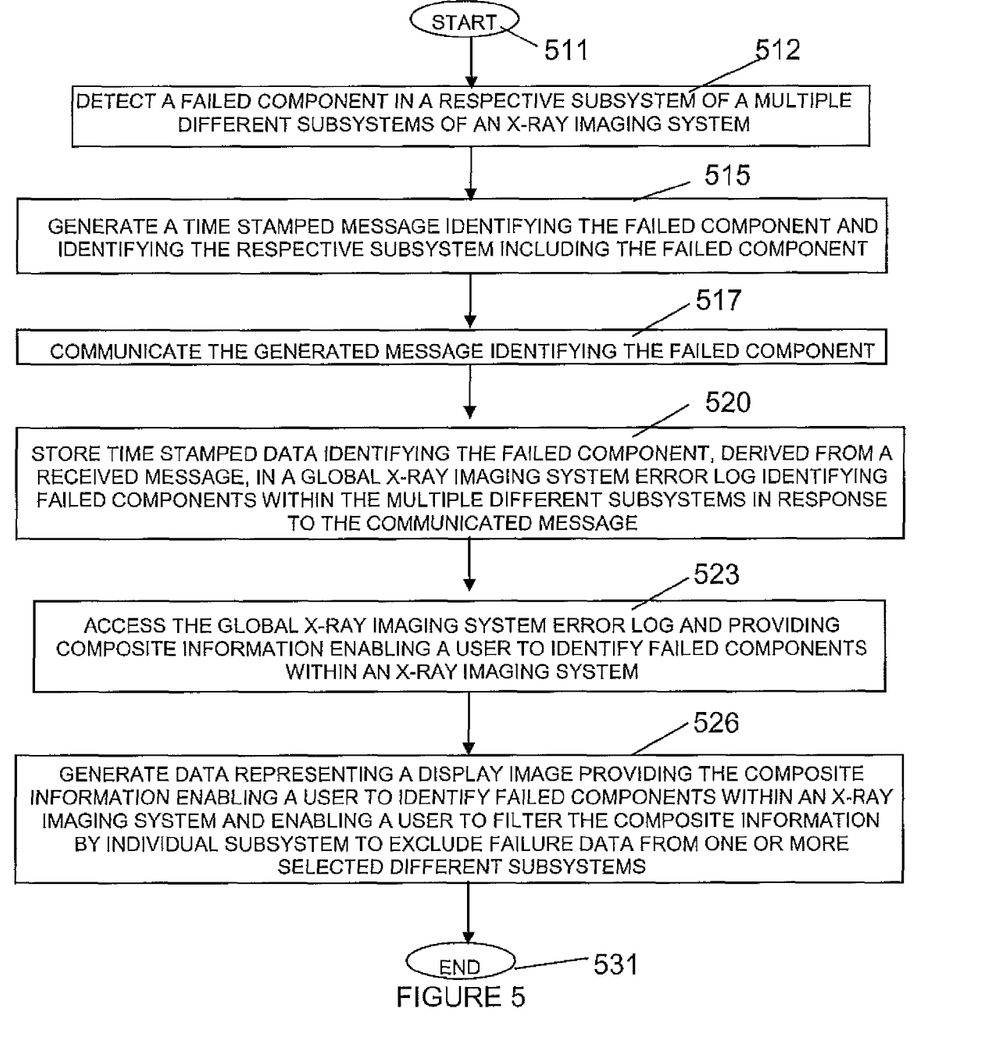
FIG. 5 shows a flowchart of a process used by a system for automatically detecting and identifying failed components of a distributed X-ray imaging system, according to invention principles.

FIG. 5 shows a flowchart of a process used by system 10 (FIG. 2) for automatically detecting and identifying failed components of distributed X-ray imaging system 100 (FIG. 1). In step 512 following the start at step 511, an executable procedure detects a failed component in a respective subsystem of multiple different subsystems of an X-ray imaging system. A communication interface in step 515 generates a time stamped message identifying the failed component and identifying the respective subsystem including the failed component. The message includes data identifying status of a component and a textual description of the failure of the failed component. The communication interface in step 517 communicates the generated message identifying the failed component. The communication interface adaptively generates and communicates, (a) error messages identifying failed subsystem components and identifying a subsystem including a failed component and (b) status messages indicating subsystem status. The subsystem status comprises at least one of, operational, in maintenance and inactive, status. In one embodiment, the communication interface initiates generation and communication of the message in an sRIO compatible format message.

In step 520 error processor 203 stores time stamped data identifying the failed component, derived from a received message, in a global X-ray imaging system error log (a repository in unit 203 or 245) in response to the communicated message. The global X-ray imaging system error log identifies time stamped subsystem component failures and failed components within the multiple different subsystems. In step 523 error processor 203 accesses the global X-ray imaging system error log and provides composite information enabling a user to identify failed components within X-ray imaging system 100. The data stored in the global system error log advantageously highlights linked failures across different X-ray imaging system subsystems and error processor 203 identifies the linked failures across different subsystems based on sequential time of failure occurrence using failure timestamps. Error processor 203 provides a composite single display image to a user identifying failed components within the X-ray imaging system. The error processor also provides a composite single display image to a user identifying status of subsystems within the X-ray imaging system including at least one of, operational, in maintenance and inactive, status.

A display processor in display 44 (or units 203 or 245) in step 526 generates data representing a display image providing the composite information enabling a user to identify failed components within an X-ray imaging system and enabling a user to filter the composite information by individual subsystem to exclude failure data from one or more selected different subsystems. The process of FIG. 5 terminates at step 531.

A processor as used herein is a device for executing machine-readable instructions stored on a computer readable medium, for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a computer, controller or microprocessor, for example, and is conditioned using executable instructions to perform special purpose functions not performed by a general purpose computer. A processor may be coupled (electrically and/or as comprising executable components) with any other processor enabling interaction and/or communication therebetween, A user interface processor or generator is a known element comprising electronic circuitry or software or a combination of both for generating display images or portions thereof. A user interface comprises one or more display images enabling user interaction with a processor or other device.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A user interface (UI), as used herein, comprises one or more display images, generated by a user interface processor and enabling user interaction with a processor or other device and associated data acquisition and processing functions.

The UI also includes an executable procedure or executable application. The executable procedure or executable application conditions the user interface processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity.

The system and processes of FIGS. 1-5 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. A system error processing unit automatically detects and identifies failed components of subsystems of a distributed X-ray imaging system and generates a global system error log identifying time stamped subsystem component failures and highlighting linked failures across different subsystems (linked by sequential time of failure occurrence) facilitating originating failure identification and being filterable by individual subsystem. Further, the processes and applications may, in alternative embodiments, be located on one or more (e.g., distributed) error processors on a network linking the units of FIG. 1. Any of the functions and steps provided in FIGS. 1-5 may be implemented in hardware, software or a combination of both.

What is claimed is:

1. A system for automatic detection and identification of failed components of a distributed X-ray imaging system, comprising:
    a plurality of different subsystems of an X-ray imaging system individually including,
        an executable procedure for detecting a failed component in a respective subsystem and
        a communication interface for initiating generation and communication of a message identifying said failed component and identifying said respective subsystem including said failed component using routing information received from a network management unit;
    a repository of data for storing data identifying failed components within said plurality of different subsystems in response to the communicated message; and
    an error processor for accessing said repository of data and providing composite information enabling a user to identify failed components within an X-ray imaging system using time sequenced error messages and using additional information concerning failed system components that may or may not have contributed to failure of a particular failing component.

2. A system according to claim 1, wherein
said communication interface employs network transport logic to support seamless operation irrespective of network topology and implementation for acquiring said routing information and
said communication interface initiates generation and communication of said message in an sRIO compatible format message.

3. A system according to claim 1, wherein
said error processor stores data in a global system error log identifying time stamped subsystem component failures.

4. A system according to claim 3, wherein
the data stored in said global system error log highlights linked failures across different X-ray imaging system subsystems.

5. A system according to claim 4, wherein
said error processor identifies said linked failures across different subsystems based on sequential time of failure occurrence using failure timestamps.

6. A system according to claim 3, including
a display processor for generating data representing a display image providing said composite information enabling a user to identify failed components within an X-ray imaging system and enabling a user to filter said composite information by individual subsystem to exclude failure data from one or more selected different subsystems.

7. A system according to claim 1, wherein
said message includes a textual description of the failure of said failed component.

8. A system according to claim 1, wherein
said message includes data identifying status of a component.

9. A system according to claim 1, wherein
said error processor provides a composite single display image to a user identifying failed components within said X-ray imaging system.

10. A system according to claim 9, wherein
said error processor provides a composite single display image to a user identifying status of subsystems within said X-ray imaging system including at least one of, (a) operational, (b) in maintenance and (c) inactive.

11. A system according to claim 1, wherein
said repository of data comprises an error log.

12. A system for automatic detection and identification of failed components of a distributed X-ray imaging system, comprising:
    a plurality of different subsystems of an X-ray imaging system individually including,
        an executable procedure for detecting a failed component in a respective subsystem and
        a communication interface for initiating generation and communication of a message identifying said failed component and identifying said respective subsystem including said failed component using routing information received from a network management unit;

a global X-ray imaging system error log for storing time stamped data identifying failed components within said plurality of different subsystems in response to the communicated message; and an error processor for accessing said global system X-ray imaging system error log and providing composite information enabling a user to identify failed components within an X-ray imaging system using time sequenced error messages and using additional information concerning failed system components that may or may not have contributed to failure of a particular failing component.

13. A system according to claim 12, wherein
the data stored in said global system error log highlights linked failures across different X-ray imaging system subsystems and
said error processor identifies said linked failures across different subsystems based on sequential time of failure occurrence using failure timestamps.

14. A system according to claim 12, wherein
said communication interface employs network transport logic to support seamless operation irrespective of network topology and implementation for acquiring said routing information and adaptively generates and communicates,
  (a) error messages identifying failed subsystem components and identifying a subsystem including a failed component and
  (b) status messages indicating subsystem status.

15. A system according to claim 14, wherein
said subsystem status comprises at least one of, (a) operational, (b) in maintenance and (c) inactive, status.

16. A method for automatic detection and identification of failed components of a distributed X-ray imaging system, comprising the activities of:
    detecting a failed component in a respective subsystem of a plurality of different subsystems of an X-ray imaging system;
    generating a time stamped message identifying said failed component and identifying said respective subsystem including said failed component;
    receiving routing information received from a network management unit
    communicating the generated message identifying said failed component using the received routing information;
    storing time stamped data identifying said failed component, derived from a received message, in a global X-ray imaging system error log identifying failed components within said plurality of different subsystems in response to the communicated message; and
    accessing said global X-ray imaging system error log and providing composite information enabling a user to identify failed components within an X-ray imaging system using time sequenced error messages and using additional information concerning failed system components that may or may not have contributed to failure of a particular failing component.

17. A method according to claim 16, including the activity of
    employing network transport logic to support seamless operation irrespective of network topology and implementation for acquiring said routing information.

* * * * *